United States Patent [19]

Tafesh et al.

[11] Patent Number: 5,041,669

[45] Date of Patent: Aug. 20, 1991

[54] PROCESS FOR THE PREPARATION OF ARYLALKYLAMINES AND SUBSTITUTED ARYLALKYLAMINES

[75] Inventors: Ahmed M. Tafesh; Graham M. Mott, both Corpus Christi, Tex.

[73] Assignee: Hoechst Celanese Corporation, Somerville, N.J.

[21] Appl. No.: 598,486

[22] Filed: Oct. 16, 1990

[51] Int. Cl.$^5$ ............................................. C07C 209/40
[52] U.S. Cl. ................................... 564/337; 564/258; 564/374; 564/383
[58] Field of Search ....................... 564/337, 374, 383

[56] References Cited

U.S. PATENT DOCUMENTS

| | | |
|---|---|---|
| 1,995,709 | 3/1935 | Hartung . |
| 2,505,645 | 4/1950 | McPhee . |
| 2,567,906 | 9/1951 | Hartung . |
| 2,784,228 | 3/1957 | Hartung . |
| 3,028,429 | 4/1962 | Wilbert et al. . |
| 3,966,813 | 6/1976 | Satzinger et al. . |
| 4,055,664 | 10/1977 | Skibbe ................................ 564/337 |
| 4,104,383 | 8/1978 | Krausz ............................... 564/337 |
| 4,277,471 | 7/1981 | Lacefield et al. .................. 564/337 |

FOREIGN PATENT DOCUMENTS

| | | | |
|---|---|---|---|
| 0022630 | 2/1980 | Japan ................................. | 564/381 |
| 0667545 | 6/1979 | U.S.S.R. ............................ | 564/374 |

OTHER PUBLICATIONS

Cannon, J. G., et al., "Conformationally Restricted Congeners of Dopamine Derived from 2-Aminoindan".
J. Med. Chemistry, vol. 25, pp. 1442 et seq. (1982).
Wellcome Physiological Research Laboratories J. Chem. Soc., vol. 95, p. 1127 (1909).
Buck, J. S., J. Am. Chem. Soc., vol. 55, p. 3389 (1933).
Umezi, M. et al., Hakko Kogaku Kaishi, vol. 55 (2) pp. 68-74 (1977).

Primary Examiner—Richard L. Raymond
Attorney, Agent, or Firm—Rosenblatt & Associates

[57] ABSTRACT

Arylalkylamines (as a sulfate salt) e.g. tyramine sulfate, are prepared by reacting substituted or unsubstituted arylalkylketones with a lower alkylnitrite in the presence of hydrogen chloride in a dipolar aprotic solvent, then combining the reaction mixture with water and extracting it with a lower alkyl ester or alcohol to recover an aryl-α-oximinoalkylketone extract. The extract, combined with a supported hydrogenation catalyst (e.g. palladium on carbon) in a nonaqueous reaction medium of a major proportion of a mildly protic carboxylic acid (e.g. acetic acid) and a minor proportion of a strong inorganic acid (e.g. sulfuric acid), which is effective in the presence of the catalyst for secondary alcohol dehydration and active as an absorbant for water produced in the dehydration reaction, is hydrogenated to produce the arylalkylamine sulfate sale.

11 Claims, No Drawings

1

PROCESS FOR THE PREPARATION OF ARYLALKYLAMINES AND SUBSTITUTED ARYLALKYLAMINES

BACKGROUND OF THE INVENTION

This invention relates to a process for the preparation of substituted or unsubstituted arylalkylamines from substituted or unsubstituted arylalkyl ketones by nitrosation to form an aryl o-oximinoalkylketone followed by hydrogenation reduction of the oximino group to an amine and dehydroxylation of an hydroxyl group produced by hydrogenation reduction of the keto group.

Substituted and unsubstituted arylalkylamines are chemical intermediates of great importance. They are used in the preparation of pharmacologically active compounds and in some instances are themselves pharmacologically active. For example, phenethylamine and p-hydroxyphenethylamine (tyramine) have sympathomimetic (adrenergic) action. Tyramine also is a moiety in opiates, and is useful as an intermediate or substituent in the preparation of other physiologically active compounds or compositions. Hydroxyltyramine (dopamine) is a physiologically important neural inhibitory transmitter.

In U.S. Pat. Nos. 1,995,709 and 2,567,906 by Hartung, a multi-operations procedure for the preparation of substituted phenylpropanol amines is described, particularly, for 1-(p- or m-hydroxyphenyl)-2-amino-1-propanol (in U.S. Pat. No. 1,995,709), and 1-(p-aminophenyl)2-amino-1-propanol (in U.S. Pat. No. 2,507,906). In U.S. Pat. No. 1,995,709, p- or m-hydroxypropiophenone is reacted with a lower alkyl nitrite in ether in the presence of hydrogen chloride to produce p- or m-hydroxyisonitrosopropiophenone, which then is separated from the reaction mixture by alkaline extraction and recovered from the alkaline solution by precipitation induced by acidification of the extract, after which the precipitate is recrystallized. The p- or m-hydroxyisonitrosopropiophenone thus separated is then reacted with hydrogen in the presence of palladium on charcoal in absolute alcohol containing dry hydrogen chloride until reduction stops, after which the amino ketone is recovered as a filtrate. The filtrate is dryed and purified by recrystallization. Then the amino ketone is dissolved in water and reacted with hydrogen in the presence of palladium on charcoal. The reaction product is recovered as the hydrochloride of the amino alcohol, for example, the hydrochloride of 1-(p-hydroxyphenyl)-2-aminopropanol (in U.S. Pat. No. 1,995,709) and the hydrochloride of 1-(p-aminophenyl)-2-aminopropanol (in U.S. Pat. No. 2,507,906).

In U.S. Pat. No. 2,505,645 by McPhee, the acidic catalytic hydrogenation process described by Hartung is employed in a method of preparing α-phenyl-β-hydroxyphenyl-β-hydroxyethylamine.

U.S. Pat. No. 2,784,228 by Hartung describes an also partially aqueous alternative process for the catalytic reduction of α-oximino ketones, using alkaline solutions instead of acidic solutions to obtain a desired amino alcohol. Difficulties and shortcomings of the acidic catalytic reduction process described by Hartung in U.S. Pat. Nos. 1,995,709 and 2,567,906 are detailed by Hartung in U.S. Pat. No. 2,784,228 and also by Wilbert et al. in U.S. Pat. No. 3,028,429. In U.S. Pat. No. 3,028,429, Wilbert et al. describe a process for the hydrogenation of isonitrosopropiophenone to produce 1-phenyl-2-aminopropanol which is a modification said to improve yields respecting the general process described by Hartung in U.S. Pat. Nos. 1,995,709 and 2,567,906.

In U.S. Pat. No. 3,966,813 by Satzinger et al. hydroxyacetophenone is reacted with a lower alkyl nitrite in a dipolar aprotic solvent in the presence of a hydrogen chloride catalyst to form m- or p-hydroxyisonitrosoacetophenone. The reaction mixture containing the isonitroso compound is poured into ice water and extracted with ethyl acetate. The ethyl acetate solution is dried, cleaned with charcoal, filtered, and vacuum distilled to recover the compound. After recrystallization, the compound is then catalytically hydrogenated to reduce the isonitroso and keto moieties of the hydroxyisonitrosoacetophenone to form 1-(m- or p-hydroxyphenyl)-2-amino-1-ethanol. The catalytic hydrogenation disclosed is conducted in an aqueous ethanol solution in the presence of hydrochloric acid in aqueous solution using a palladium on charcoal catalyst.

In a procedure described by Cannon, J. G. et al. in *J. Med. Chem.*, V.25, p. 1442 (1982), 4, 5-dimethoxy-1-indanone is reacted with n-butylnitrite in methanol and upon acidification with HCl, 4,5-dimethoxy-2-oximino-1-indanone is recovered as a precipitate. This is added to a major amount of glacial acetic acid and a minor amount of concentrated sulfuric acid and hydrogenated over a palladium on carbon catalyst to produce 4,5-dimethoxy-2-aminoindan hydrochloride, which is then recovered.

Tyramine is described in the literature as produced by the sodium in ethanol reduction of p-hydroxyphenylmethyl cyanate, *J. Chem. Soc.* v.95, p.1127 (1909); by the platinum catalyzed hydrogenation of p-hydroxyphenylmethylcyanate, Buck J. S., *J. Am. Chem Soc.* v.55, p.3389 (1933); and by a lactobacillus decarboxylation of 1-(p-hydroxyphenyl)-2-aminopropionic acid, Umezi, M. et al., *Hakko Kooaku Kaishi.* v.55(2), p.68–74 (1977).

The following U.S. Patents involve various aspects of hydroxyphenethylamine or tyramine but do not disclose the process of this invention: U.S. Pat. Nos. 4,885,312; 4,868,218; 4,868,132; 4,861,800; 4,857,522; 4,762,781; 4,699,782; 4,686,179; 4,623,485; 4,609,544; 4,563,263; 4,515,773; 4,503,147; 4,496,655; 4,465,775; 4,436,828; 4,370,495; 4,277,460; 4,207,308; 4,190,593; 4,175,136; 4,032,406; 3,997,608; 3,997,525; 3,993,436; 3,981,982; 3,932,461; 3,894,051; 3,818,015; 3,676,447; 3,576,808; 3,457,354; and 2,695,297.

DETAILED DESCRIPTION OF THE INVENTION

In accordance with this invention, a process is provided for the preparation of arylalkylamines, which comprises (1) reacting an arylalkylketone of the formula

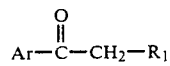

in which $R_1$ represents hydrogen or a $C_1$–$C_5$ alkyl or cycloalkyl and Ar represents an aromatic phenyl or naphthyl radical unsubstituted or substituted with one or more substituents selected from the group of amino, alkylamino, dialkylamino, hydroxyl, alkoxy, alkyl, phenyl, benzyl, aryloxy, sulfonic acid, and sulfinic acid radicals, wherein the alkyl in the alkyl containing substituent(s) is a branched or unbranched $C_1$–$C_5$ alkyl radical and any of such alkyl and the phenyl and benzyl radicals may be optionally substituted with one or more substituents selected from amino, hydroxyl, sulfonic acid, and sulfinic acid radicals, the phenyl and benzyl substituents also or alternatively being optionally substituted with one or more $C_1$–$C_5$ alkyl or $C_1$–$C_5$ alkoxy, or both, radicals, with a lower alkyl nitrite in the presence of hydrogen chloride in a dipolar aprotic solvent to produce a reaction mixture which includes an aryl-α-oximinoalkyl ketone reaction product; (2) combining said reaction mixture with water and extracting the aryl-α-oximinoalkyl ketone from the aqueous reaction mixture with an organic solvent selected from lower alkyl esters and lower alkyl alcohols to produce an aryl-α-oximinoalkyl ketone extract solution free of water; (3) combining the extract solution with (a) a hydrogenation catalyst selected from platinum, palladium, nickel, cobalt, and ruthenium or mixtures thereof on an inert support, and (b) a non-aqueous liquid including (i) a major proportion of a carboxylic acid having a $pK_a$ of from about 1 to 5 which is a solvent for said aryl-α-oximinoalkyl ketone, and (ii) a minor proportion of a strong inorganic acid effective for secondary alcohol dehydration in the presence of the aforesaid catalyst and of such amount as to absorb substantially all of the water produced in the secondary alcohol dehydration reaction, to form a reaction mixture; (4) contacting the reaction mixture with hydrogen to produce a salt of the strong acid and an arylalkylamine derived from said aryl-αoximinoalkylamine; and (5) recovering the arylalkylamine salt from the reaction mixture.

Examples of arylalkyl ketones usable in the process of this invention, and in which the aryl of the arylalkylketone is an unsubstituted phenyl or naphthyl radical, are acetophenone and acetonaphthone, and in which the aryl is a substituted phenyl or naphthyl radical, are o-, m- and p-hydroxyacetophenone, o-, m- and p-methylacetophenone, p-ethylacetophenone, p-propylacetophenone, p-butylacetophenone, o-, m- and p-methoxyacetophenone, o-, m- and p-ethoxyacetophenone, 2,4-methoxyacetophenone, p-phenylacetophenone, 2-methoxy-4-methylacetophenone, α-acetonaphthone, acetonapthone, β-acetonapthone, propiophenone, o- and p-methoxypropiophenone, p-methylpropiophenone, p-ethylpropiophenone, butyrophenone, p-methylbutyrophenone, p-methoxybutyrophenone, valerophenone and p-methylvalerophenone, p-acetamidopropiophenone, p-benzylaminopropiophenone, p-benzoylaminopropiophenone, p-aminoacetophenone, 1-(p-aminophenyl)propiophenone, p- and m-hydroxyphenylacetophenone, p- and m-hydroxyphenylpropiophenone, benzyl 3,4-dibenzyloxyphenylketone, benzyl p-benzyloxyphenylketone, 1-(4-methylphenyl)propiophenone, and p-phenylsulfonylacetophenone, 4,5 dihydroxy-1-indanone, 5,6-dihydroxy-1-indanone, 4,5 dimethoxy-1-indanone and 5,6-dimethoxy-1-indanone.

In accordance with this invention, an arylalkylketone of the above and foregoing formula is reacted with a lower alkylnitrite in the presence of hydrogen chloride in a dipolar aprotic solvent. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide and hexamethylphosphoric acid triamide (HMPT). Suitable alkyl nitrites are lower alkyl nitrites in which the alkyl radical has from 1 to 5 carbon atoms; for example, methylnitrite, ethylnitrite, isopropylnitrite, n-butylnitrite nitrite, t-butylnitrite, and the like. The reaction of the ketone with the lower alkyl nitrite suitably can be carried but at a temperature in the range from $-30°$ C. to $100°$ C., preferably in the range from $10°$ C. to $50°$ C. The amount of hydrogen chloride used suitably is from about 0.5 to 1.2 equivalents, relative to the ketone used. Respecting suitable dipolar aprotic solvents and lower alkyl nitrites and conditions for this aspect of the invention, reference is made to U.S. Pat. No. 3,966,813.

Protic by-products of the dipolar aprotic solvents, for example, amine by-products of DMF, interfere with the efficacy or poison the hydrogenation catalysts employed in this invention. Differential extraction of the reaction mixture containing the aryl-α-oximinoketone is essential to remove the amine by-product. The reaction mixture is combined with water, preferably ice, and extracted with multiple volumes of an organic solvent in which the aryl-α-oximinoketone is preferentially soluble relative to amines. Suitably the organic solvent is a lower alkyl ester and lower alkyl alcohol, for example, methylacetate, ethylacetate, propylacetate, or ethanol, propanol, or n-butanol.

The mildly protic carboxylic acid solvent employed in the nonaqueous reaction medium has an ionization constant, expressed as a $pK_a$, in the range from about 1 to about 5. To be suitable, the solvent must have a melting point and boiling point placing it in the liquid state under the conditions employed for the hydrogenation and secondary alcohol dehydration reactions of the process. Preferably, the solvent is an alkylcarboxylic acid having a $pK_a$ of about 5; for example, formic acid ($pK_a$ 3.75), acetic acid ($pK_a$ 4.7), propanoic acid ($pK_a$ 4.9), butanoic acid ($pK_a$ 4.81), 2-methylpropanoic acid ($pK_a$ 4.8) (isobutyric acid), pentanoic acid ($pK_a$ 4.89), 2-2-dimethylpropanoic acid ($pK_a$ 5.1)(pivalic acid), and heptanoic acid ($pK_a$ 4.9) all are suitable. Acetic acid is most preferred.

Under mildly protic conditions in the presence of the hydrogenation catalyst, hydrogen contacted with the aryl-α-oximinoketone hydrogenates the aryl-α-oximinoketone to an amino alcohol. Prolonged contact of the carboxylic acid with the amino alcohol under elevated heating conditions, for example, under reflux, is to be avoided if it is not desired to alkylate the amine group. For example, it is known to react an arylaminopropanol with formic acid in aqueous formaldehyde at elevated temperatures to methylate the amine, as in U.S. Pat. 2,921,092.

The strong inorganic acid which forms the other constituent of the nonaqueous reaction medium is a strong inorganic acid effective for secondary alcohol dehydration in the presence of the hydrogenation catalyst. It is an acid which is an absorbent of water of reaction produced in the dehydration reaction, and preferably is sulfuric acid or phosphoric acid. Use of a hydrogenation reaction medium in which the solvent is nonaqueous and mildly protic, and which includes a strong inorganic acid that catalyzes cleavage of the carbon-oxygen bond of the secondary alcoholic group and absorbs the water of reaction produced under the hydrogenation conditions, produces excellent conversion of the α-oximinoketone to the corresponding alkylamine. Without being bound to a particular mechanism or explanation, it is believed that the excellent yields result from displacement of the equilibrium of the alcoholic dehydration reaction to the right as water of reaction is removed by absorption, which in turn displaces the equilibrium of the ketone-to-alcohol reduction reaction to the right.

Hydrogenation with hydrogen in the presence of the hydrogenation catalyst selected from platinum, palladium, nickel, cobalt, and ruthenium or mixtures thereof on an inert support is conducted under positive hydrogen pressures of from about 15 to about 500 psig, preferably in the range from about 45 to about 80 psig at temperatures suitably in the range from about 5° C. to about 100° C., preferably in the range from about 10° C. to about 50° C. At temperatures in the upper part of the useful range, the α-oximino-ketone conversion to alkylamine proceeds very rapidly and, generally speaking, better reaction control is realized in the preferred temperature range. At temperatures above 100° C., yields of the unsubstituted alkylamine are decreased by alkylation from the carboxylic acid solvent.

The reaction medium has a major part of the carboxylic acid and a minor part of the strong inorganic acid that is an absorbent for water. Sulfuric acid at elevated temperatures produces alkenes from secondary alcohols, and the proportion of the strong inorganic water absorbent acid used must be considered in the context of temperature and hydrogen pressure. In general, by minor part of strong inorganic acid is meant not more than about 40 percent by volume of the inorganic acid to the organic carboxylic acid; preferably, from about 10 to about 30 parts of carboxylic acid per part of inorganic acid are employed. Preferably the reaction medium is from about 10 to about 50 ml per gram weight of the isonitrosoketo compound, or arylalkylketo compound, used as the isonitrosoketone precursor.

The following example illustrates the invention, and is not to be understood as limiting the invention only to this embodiment.

EXAMPLE I

To a 3-neck 2 L flask is added 2.2 moles of dry HCl to 1000 ml of dry dimethyl formamide (DMF). To the flask is then added 272 grams (2 moles) of p-hydroxyacetophenone all at once. Then, 296 ml grams (2.2 moles) of 90% tertiary butyl nitrite is added very slowly so as to maintain the reaction medium temperature at about 40° C., which takes about 2 hours, after which the reaction medium is stirred for an additional 3 hours while maintaining the temperature at about 40°–45° C. The contents of the flask are then poured into one liter of ice and extracted three times with 200 ml of ethyl acetate. About 200 ml of the crude, dry ethyl acetate solution is then added with 10.5 grams of 5% palladium/carbon catalyst to a reaction medium solution made by combining 350 ml glacial acetic acid and 35 ml of concentrated sulfuric acid. The reaction mixture is then placed in one liter autoclave reactor and degassed 3 times with nitrogen gas, then 3 times with hydrogen gas, after which the reactor is pressurized to 100 psig with hydrogen gas and the reaction is monitored over a period of 7 hours as follows:

| Time (min.) | Temperature (°C.) | Reactor Pressure (psig) | Surge Vessel Pressure (psig) |
| --- | --- | --- | --- |
| 0 | 44.8 | 100 | 457 |
| 30 | 37.2 | 100 | 447 |
| 75 | 35.0 | 100 | 395 |
| 95 | 33.0 | 100 | 382 |
| 130 | 31.0 | 100 | 350 |
| 165 | 29.4 | 100 | 345 |
| 420 | 23.9 | 100 | 313 |

The reaction mixture from the reactor is then filtered to recover the catalyst, and the filtrate is concentrated to recover Tyramine.H2SO4 in 64% yield.

Having described our invention, what we claim is:

1. A process for the preparation of an arylalkylamine, which comprises:

reacting a compound of the formula

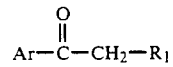

wherein $R_1$ = hydrogen or a $C_1$-$C_5$ alkyl or cycloalkyl, and
Ar = an aromatic phenyl or naphthyl radical unsubstituted or substituted with one or more substituents selected from the group of amino, alkylamino, dialkylamino, hydroxyl, alkoxy, alkyl, phenyl, benzyl, sulfonic acid, and sulfinic acid radicals, wherein the alkyl in the alkyl containing substituent(s) is a branched or unbranched $C_1$-$C_5$ alkyl radical and any of such alkyl and said phenyl and benzyl radicals are optionally substituted with one or more substituents selected from amino, hydroxyl, sulfonic acid, and sulfinic acid radicals, and said phenyl and benzyl substituents are optionally substituted with a $C_1$-$C_5$ alkyl or $C_1$-$C_5$ alkoxy radical, or both, with a lower alkylnitrite in the presence of hydrogen chloride in a dipolar aprotic solvent to produce a reaction mixture which includes an aryl-α-oximinoalkyl ketone derived from said compound, combining said reaction mixture with water and extracting said aryl-α-oximinoalkyl ketone from said aqueous reaction mixture with an organic solvent selected from lower alkyl esters and lower alkyl alcohols to produce an aryl-α-oximinoalkyl ketone extract solution free of water, combining said extract solution with (a) a hydrogenation catalyst selected from platinum, palladium, nickel, cobalt, and ruthenium or mixtures thereof on an inert support, and (b) a nonaqueous liquid including (i) a major proportion of a carboxylic acid having a $pK_a$ of from about 1 to 5 which is a solvent for said aryl-α-oximinoalkyl ketone, and (ii) a minor proportion of a strong inorganic acid effective for secondary alcohol dehydration in the presence of said catalyst and of such amount as to absorb substantially all of the water produced in the secondary alcohol dehydration reaction, to form a reaction mixture, contacting said reaction mixture with hydrogen to produce a salt of said strong acid and an arylalkylamine derived from said aryl-α-oximinoalkylamine, and recovering the arylalkylamine salt from said reaction mixture.

2. The process of claim 1 in which said carboxylic acid is acetic acid.

3. The process of claim 1 in which said strong inorganic acid is sulfuric acid or phosphoric acid.

4. The process of claim 3 in which said carboxylic acid is acetic acid.

5. The process of claim 4 in which said reaction mixture is contacted with hydrogen under pressures of from about 15 to about 500 psig at temperatures in the range from about 5° C. to about 100° C.

6. The process of claim 5 in which said liquid is from about 10 to about 30 parts of acetic acid per part of inorganic acid.

7. The process of claim 6 in which the said inorganic acid is sulfuric acid.

8. The process of claim 7 in which said liquid is from about 10 to about 50 ml per gram weight of said compound.

9. The process of claim 8 in which said compound is p-hydroxyacetophenone and said arylalkylamine is p-hydroxyphenethylamine.

10. The process of claim 1 in which said compound is p-hydroxyacetophenone and said arylalkylamine is p-hydroxyphenethylamine.

11. A process for the preparation of the sulfuric salt p-hydroxyphenethylamine which comprises:
reacting p-hydroxyacetophenone with a lower alkylnitrite in the presence of hydrogen chloride in a dipolar aprotic solvent to produce a reaction mixture containing p-hydroxyisonitrosoacetophenone,
combining said reaction mixture with water and extracting said p-hydroxyisonitrosoacetophenone with ethylacetate to get a solution of p-hydroxyisonitrosoacetophenone,
combining said solution with a palladium catalyst on a carbon support in a reaction medium of a major proportion of acetic acid and a minor proportion of sulfuric acid, contacting said reaction medium with hydrogen under pressures of from about 15 to about 500 psig at temperatures in the range from about 5° C. to about 100° C. to produce the sulfuric salt of tyramine, and
recovering said salt from said reaction medium.

* * * * *